US00PP18721P2

(12) United States Plant Patent
Utecht

(10) Patent No.: US PP18,721 P2
(45) Date of Patent: Apr. 8, 2008

(54) ***PELARGONIUM* PLANT NAMED 'GRAMON '**

(50) Latin Name: *Pelargonium×hortorum*
Varietal Denomination: Gramon

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/506,134

(22) Filed: Aug. 17, 2006

(51) Int. Cl.
*A01H 5/00* (2006.01)

(52) U.S. Cl. ..... Plt./327

(58) Field of Classification Search ..... Plt./327
See application file for complete search history.

(56) References Cited

PUBLICATIONS

UPOV–ROM GTITM, Plant Variety Database, Jan. 2007, GTI Jouve Retrieval Software, Citation for Pelargonium 'Gramon 'and 'Fiv 277 ', 2 pages.*
Flora–Nova Pflanzen GmbH [retrieved on Ju. 30, 2007]. Retrieved from the Internet:<http://www.top500.de/details/475/flora–nova_pflanzen_gmbh_germany.php>2 pages.*

* cited by examiner

*Primary Examiner*—Kent Bell
*Assistant Examiner*—June Hwu
(74) *Attorney, Agent, or Firm*—Jondle & Associates, P.C.

(57) ABSTRACT

A new cultivar of *pelargonium* particularly characterized by having salmon-orange, single, stellar-type flowers with relatively long peduncles, floriferous with medium-sized inflorescences borne well-above the foliage, medium-green foliage with strong zonation, a medium to tall-sized, rounded and well-branched plant habit, an early and continuous flowering response and good resistance to rain, is disclosed.

1 Drawing Sheet

Genus and species: *Pelargonium×hortorum.*
Variety denomination: 'Gramon'.

BACKGROUND OF THE NEW PLANT

The present invention comprises a new and distinct cultivar of *pelargonium,* botanically known as *Pelargonium× hortorum,* and hereinafter referred to by the cultivar name 'Gramon'. The new cultivar is a product of a planned breeding program which had the objective of creating new varieties having stellar-type flowers, medium-green foliage, medium-sized and well branching plants in a variety of flower colors. 'Gramon' was discovered as a seedling resulting from the cross of the female parent 'K99-4006-2' (unpatented), proprietary *pelargonium* plant having light-salmon, single-type flowers and the male parent 'K00-5035-15' (unpatented), a proprietary *pelargonium* plant having pink double flowers.

The new cultivar was created in 2001 in Hillscheid, Germany and has been asexually reproduced repeatedly by vegetative cuttings in Galdar, Gran Canaria, Spain, and Hillscheid, Germany over a four-year period. 'Gramon' has been found to retain its distinctive characteristics through successive asexual propagations, 'Gramon' reproduces true to type in successive generations of asexual reproduction.

Plant Breeder's Rights for this cultivar were applied for in Germany on Apr. 4, 2005 and Canada on Apr. 20, 2005.

SUMMARY OF THE INVENTION

The following are the most outstanding and distinguishing characteristics of this new cultivar when grown under normal horticultural practices in Hillscheid, Germany.

1. Single, stellar-type, salmon-orange flowers with relatively long peduncles;

2. Floriferous with medium-sized inflorescences well-above the foliage;
3. Medium-green foliage with strong zonation;
4. Medium-sized or taller plant habit;
5. A rounded, well-branched and bushy plant habit;
6. Good rain resistance; and
7. An early and continuous flowering response.

DESCRIPTION OF THE PHOTOGRAPH

This new *pelargonium* plant is illustrated by the accompanying photograph which shows overall plant habit including inflorescences, buds, and foliage of the plant; the colors shown are as true as can be reasonably obtained by conventional photographic procedures. The photograph is of an about 14-week-old, un-pinched plant grown from rooted cuttings, in 12-cm pots and grown under greenhouse and outdoor conditions which approximate those generally used in commercial practice.

DESCRIPTION OF THE NEW CULTIVAR

The following detailed description sets forth the distinctive characteristics of 'Gramon'. The data which define these characteristics were collected from asexual reproductions carried out in Hillscheid, Germany. The plant history was taken on 12-week old, un-pinched plants in 12-cm pots in a greenhouse during late May. Color readings were taken under natural light in late May from flowers grown in the greenhouse. Color references are primarily to the RHS Colour Chart of The Royal Horticultural Society of London (RHS) (2001).

DETAILED BOTANICAL DESCRIPTION

Classification:
*Family.*—Geraniaceae.

*Botanical.*—*Pelargonium×hortorum.*
*Common name.*—Zonal geranium, stellar type.

Parentage:
*Female parent.*—'K99-4006-2' a proprietary *pelargonium* plant having light-salmon single-type flowers (unpatented).
*Male parent.*—'K00-5035-15', a proprietary *pelargonium* plant having pink, double, stellar-type flowers (unpatented).

Plant:
*Form.*—Shrub, self-branching, rounded shape.
*Branching habit.*—6 to 8 branches per plant.
*Height* (*measured from base of the stem to the tips of the branches, excluding the inflorescence*).—19.8 cm.
*Width* (*plant diameter*).—30.2 cm.
*Time to produce a flowering plant.*—Plant had an average of one opened inflorescence about 8–9 weeks after planting rooted cuttings in Hillscheid, Germany.
*Outdoor plant performance.*—Plants continuously flower; a count in late summer in Hillscheid, Germany produced about 20 to 25 inflorescences per plant.

Leaves:
*Arrangement.*—Alternate.
*Immature leaf color.*—Medium-green. Upper surface: RHS 137C. Lower surface: RHS 137D.
*Mature leaf color.*—Upper surface: RHS 137C (medium-green). Lower surface: RHS 143A.
*Zonation color.*—Relatively strong, RHS 166A (brown) or somewhat deeper, nearly RHS N186C.
*Zonation diameter.*—Inner diameter of ring: 5.0 cm to 5.3 cm. Band or belt of zonation: 1.0 cm to 1.5 cm.
*Size.*—Length: 5.5 cm. Width: 9.0 cm.
*Shape.*—Roughly semi-circular to flabellate, with distinct lobes.
*Apex.*—Dentate with rounded tips.
*Base.*—Truncate.
*Margin.*—Dentate.
*Texture.*—Upper surface is smooth, dull, and velvety.
*Petioles.*—Color: RHS 143A. Length: 5.0 cm to 6.0 cm. Diameter: 0.2 cm to 0.3 cm. Texture: Upper surface: Covered with slight short pubescence. Lower surface: Smooth apart from the protruding veins, covered with fine pubescence.

Stems:
*Stem color.*—RHS 143C (light-green).
*Length.*—14 cm to 17 cm.
*Internode length.*—2.0 cm to 3.0 cm.
*Texture.*—Appears smooth but with very short pubescence.

Inflorescence bud: (just before petals unfold).
*Shape.*—Elliptical, narrow.
*Size.*—Length: 1.5 cm to 1.6 cm. Width: 0.5 cm to 0.7 cm.
*Color of sepals.*—RHS 143A to RHS 143B (grass-green).
*Color of petals.*—RHS 41C.

Inflorescence:
*Inflorescence type.*—An umbel composed of 20 to 30 flowers and buds.
*Umbel.*—Shape: Nearly semi-spherical. Diameter: 8.7 cm. Height (depth): 3.5 cm to 4.0 cm.
*Lastingness of umbel on the plant.*—About 16 days.
*Peduncle.*—Color: RHS 143C (light-green). Length: 24 cm. Diameter: 0.3 cm to 0.4 cm. Texture: With short pubescence.
*Pedicel.*—Color: Mainly RHS 181A to RHS 181B (reddish-brown) and RHS 143C (light-green) near the base. Length: 2.7 cm, with a spur. Diameter: 0.15 cm. Texture: Short glandular hair.

Corolla:
*Shape of corolla.*—Star-shaped with elliptical to rhomboid lower petals and very narrow upper petals, distinct gap between upper and lower petals.
*Form.*—Single.
*Diameter.*—4.5 cm.
*Number of petals.*—5.
*Petaloids.*—None.
*Lastingness of individual flowers on plant.*—8 days at 18° C.
*Fragrance.*—None.

Petals:
*Shape.*—Upper petals are lanceolate and lower petals are lanceolate to rhomboid.
*Apex.*—Broadly acute or divided.
*Base.*—Acute.
*Margin.*—Entire or slightly crenate at the tip.
*Texture.*—Upper surface: Smooth, slightly glossy. Lower surface: Glabrous.
*Upper petals.*—Length: 2.3 cm to 2.5 cm. Width: 0.3 cm to 0.6 cm. Color: Upper surface: RHS 43C. Lower surface: RHS 52C. Markings: Weak veins, RHS 52A (reddish).
*Lower petals.*—Length: 1.8 cm to 2.0 cm. Width: Up to 1.1 cm. Color: Upper surface: Between RHS 43C and RHS 43D. Lower surface: RHS 52D. Markings: Absent.

Sepals:
*Number.*—5.
*Color.*—RHS 143B (light-green) for both surfaces with an RHS 179A (brown) spot at the base.
*Length.*—0.8 cm to 0.9 cm.
*Width.*—Largest upper sepal: 0.3 cm. Other sepals: 0.1 cm to 0.2 cm.
*Shape.*—Lanceolate.
*Apex.*—Acute.
*Base.*—Fused.
*Margin.*—Entire.
*Texture.*—Upper surface: Glabrous. Lower surface: Short glandular hair with sparse long hairs.

Reproductive organs:
*Androecium.*—Number of anthers: 7. Filament length: 0.5 cm to 0.7 cm. Filament color: Mainly RHS 155D (white) to RHS 41B at the upper end. Pollen color: RHS 30A (orange). Pollen amount: Moderate.
*Gynoecium.*—Pistil: Number: 1. Length: 0.7 cm. Stigma color: RHS 46C to RHS 46D (red). Stigma shape: 5 to 6 lobed. Style color: RHS 46C (red). Style length: 0.3 cm. Style shape: Filiform (filament-like) with the lobes of the stigma. slanting outwards and reflexed.

Fruit and seed set: No seed set observed.

Disease and insect resistance: No particular resistance or susceptibility has been observed but slight susceptibility to *Botrytis* due to the double flowers.

COMPARISON WITH PARENTAL AND COMMERCIAL CULTIVARS

'Gramon' differs from the female parent 'K99-400602' (unpatented) by having deeper salmon-orange flowers, while 'K99-400602' has light-salmon colored flowers.

'Gramon' differs from the male parent 'K00-5035-15' (unpatented) by having salmon-orange and single-type flowers, while 'K00-5035-15' has pink, double flowers.

'Gramon' differs from the commercial variety 'Shalimar' (unpatented) by having salmon-orange flowers, while 'Shalimar' has light-pink flowers. In addition, 'Gramon' has a shorter plant habit and shorter peduncles than 'Shalimar'.

'Gramon' differs from the commercial comparison variety 'Sunrise Salmon Flash' (U.S. Plant Pat. No. 13,306) in that 'Gramon' has a deeper and more orange hue of flower color, while 'Sunrise Salmon Flash' has lighter, salmon-pink flowers (roughly RHS 55C and RHS 55D to RHS 52D). Additionally, 'Sunrise Salmon Flash' has somewhat smaller flowers, where the upper and lower petals are about equal size and has a more closed corolla shape (nearly no gaps between the petals).

'Gramon' differs from the commercial comparison variety 'Grasalm' (U.S. Plant Pat. No. 16,642) in that 'Gramon' has salmon-orange flowers, while 'Grasalm' has rose-red flowers.

I claim:

1. A new and distinct cultivar of *pelargonium* plant as shown and described herein.

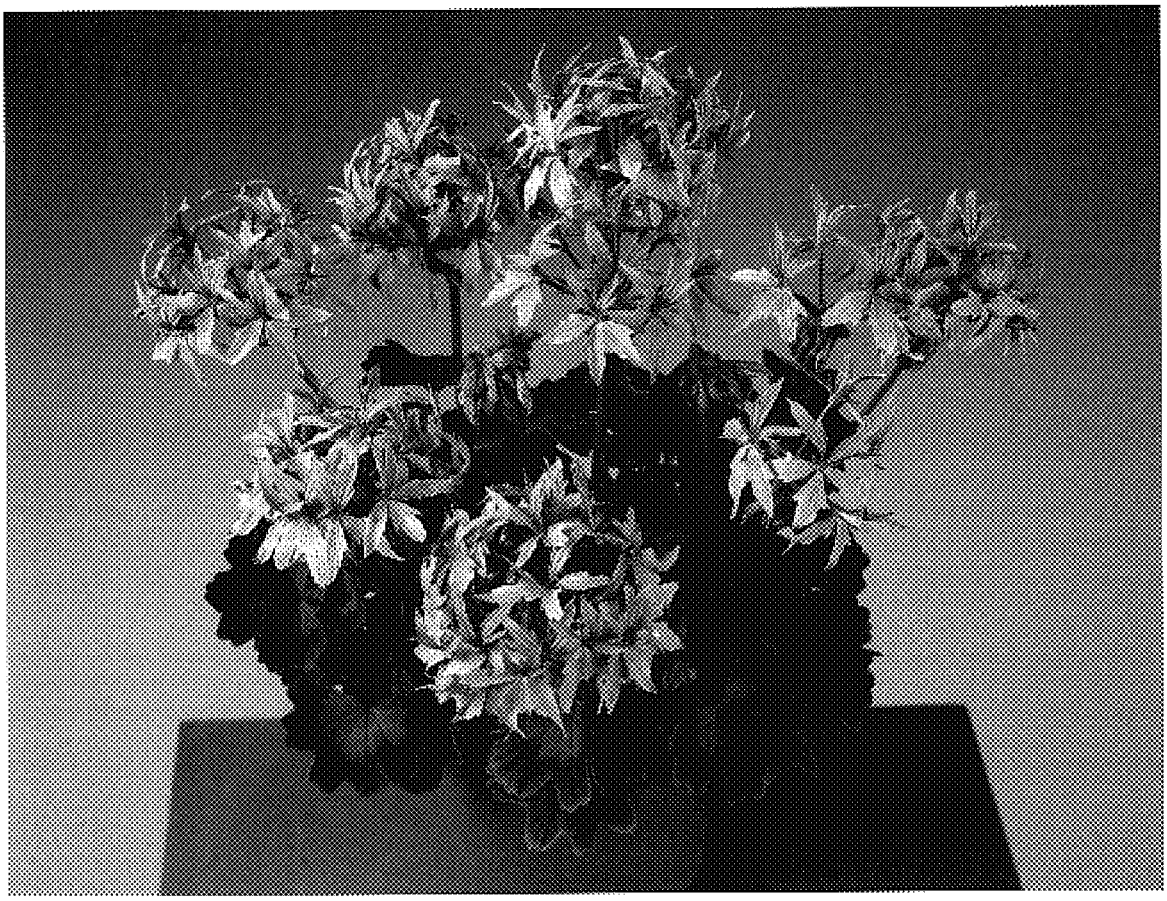

* * * * *